US00PP36275P2

(12) United States Plant Patent
Jhe

(10) Patent No.: US PP36,275 P2
(45) Date of Patent: Nov. 26, 2024

(54) ***SYNGONIUM* PLANT NAMED 'CLA 20230912'**

(50) Latin Name: *Syngonium podophyllum*
Varietal Denomination: CLA 20230912

(71) Applicant: Flores Laeti, Den Hoorn (NL)

(72) Inventor: Chen Shih Jhe, Linluo Township (TW)

(73) Assignee: Flores Laeti B.V. (NL)

( * ) Notice: Subject to any disclaimer, the term of this patent is extended or adjusted under 35 U.S.C. 154(b) by 0 days.

(21) Appl. No.: 18/426,864

(22) Filed: Jan. 30, 2024

(51) Int. Cl.
*A01H 5/12* (2018.01)
*A01H 6/10* (2018.01)

(52) U.S. Cl.
USPC ..... Plt./374

(58) Field of Classification Search
USPC ..... Plt./373, 374
See application file for complete search history.

(56) References Cited

U.S. PATENT DOCUMENTS

PP18,016 P2 * 9/2007 Strode ..... A01H 6/10
Plt./374

* cited by examiner

*Primary Examiner* — Karen M Redden
(74) *Attorney, Agent, or Firm* — Cassandra Bright

(57) ABSTRACT

A new and distinct cultivar of *Syngonium* plant named 'CLA 20230912' is disclosed, characterized by dark green-colored leaves with random bright pink and white colored splashes, flecks, and speckles. Plants are upright and symmetrical as well as bushy and dense. The new cultivar is a *Syngonium*, normally used for indoor ornamental purposes.

1 Drawing Sheet

Latin name of the genus and species: *Syngonium podophyllum.*

Cultivar denomination: 'CLA 20230912'.

BACKGROUND OF THE INVENTION

The new *Syngonium* cultivar is the result of a naturally occurring whole plant mutation of *Syngonium podophyllum* 'Pink Splash', unpatented. *Syngonium* 'CLA 20230912' was found and selected by the inventor in a nursery in Pingtung County, Taiwan in December of 2022.

Asexual reproduction of the new cultivar has been performed by vegetative cuttings. This was first performed at the same nursery in Pingtung County, Taiwan in December of 2022, and has shown that the unique features of this cultivar are stable and reproduced true to type in multiple successive generations.

SUMMARY OF THE INVENTION

The cultivar 'CLA 20230912' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CLA 20230912' These characteristics in combination distinguish 'CLA 20230912' as a new and distinct *Syngonium* cultivar:

1. Upright and symmetrical plant shape.
2. Dense and bushy plant form.
3. Dark green-colored leaves with random bright pink and green-white colored splashes, flecks, and speckles.

PARENT COMPARISON

Plants of the new cultivar *Syngonium* 'CLA 20230912' are similar to plants of *Syngonium* 'Pink Splash' in most horticultural characteristics; however, plants of the new cultivar 'CLA 20230912' differ in the following:

1. Foliage color of the new cultivar is dark green with random bright pink and green-white colored splashes, flecks, and speckles. Foliage color of the parent cultivar is medium green with dull pink splashes.
2. The new cultivar is a more compact plant than the parent variety.

COMMERCIAL COMPARISONS

Plants of the new cultivar 'CLA 20230912' are comparable to the commercial variety *Syngonium* 'Red Spot Tricolor', unpatented. The two *Syngonium* varieties are similar in most horticultural characteristics, however, the new cultivar 'CLA 20230912' differs in the following:

1. Pink coloration on foliage of the new variety is darker and brighter than the pink coloration on foliage of 'Red Spot Tricolor'.
2. Green coloration on foliage of the new variety is darker and brighter than the green coloration on foliage of 'Red Spot Tricolor'.
3. Plants of the new cultivar are more vigorous than plants of this comparator.

BRIEF DESCRIPTION OF THE PHOTOGRAPH

The accompanying photograph illustrates in full color a typical plant of the new cultivar, 'CLA 20230912' grown in a greenhouse in Pingtung County, Taiwan. Plants are approximately 12 weeks old in 9 cm pots. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6th Edition 2007 except where general terms of ordinary dictionary significance are used. The following observations and measurements describe 'CLA 20230912' plants grown in a greenhouse in Woodburn, Oregon. The growing temperature ranged from approximately 20° C. to 25° C. during the day and from approximately 18° C. to 20° C. during the night. General light conditions are normal sunlight and numerical values represent averages of typical plant types.

Botanical classification: *Syngonium podophyllum* 'CLA 20230912'.

PROPAGATION

Type of propagation typically used: Terminal vegetative cuttings.

Time to initiate roots: About 14 days at approximately 25° C.

Time to produce a rooted plantlet: About 3 weeks at approximately 22° C. to 28° C.

Root description: Primary roots fleshy, about 5 to 8 mm in diameter colored near Greyed- Orange 165D and N186C. New hairlike roots colored near RHS Green-White 157D.

PLANT

Age of plant described: 12 weeks old from a rooted cutting.

Container size: 4-inch pot.

Plant shape: Inverted triangle.

Height: Approximately 15 cm to top of highest leaf,

Plant spread: Approximately 28 cm in a 4 inch pot.

Growth rate: Approximately 12 to 13 weeks from an unrooted cuttings to a finished plant in a 4 inch pot.

Branching characteristics: No branching. Leaves emerge direct from base of plant.

Number of leaves per plant: Average range 10 to 20.

FOLIAGE

Leaf:

*Arrangement*.—Basally emerging.

*Average length (including petiole)*.—Approximately 12 cm.

*Average width*.—Approximately 8 cm.

*Shape of blade*.—Sagittate.

*Aspect*.—Flat to slightly undulate.

*Apex*.—Acute.

*Base*.—Hastate

*Margin*.—Entire.

*Texture of top surface*.—Glabrous.

*Texture of bottom surface*.—Glabrous.

*Color*.—Young foliage upper side: Near R.H.S. Red 48A and 48B. About ⅓ of emerging foliage is about ½ Green 143A and ½ Red 48A. Colors not mixed. Young foliage under side: Near R.H.S. Green 143C flushed Greyed-Red 181C. Mature foliage upper side: Near R.H.S. Red 48B, Green 137A, Green-White 157A. Colors are solid and not mixed occurring as splotches, flecks and speckles. Some larger blotches of 157A and Red 48B. Mature foliage under side: Near R.H.S. Green 137C.

Venation:

*Type*.—Palmate.

*Venation coloration upper side*.—Indistinguishable from leaf blade.

*Venation coloration under side*.—Indistinguishable from leaf blade.

Petiole (including wing):

*Length*.—Approximately 7 cm.

*Width*.—At geniculum: 7 to 8 mm. Above clump: Approximately 5 mm.

*Color*.—Near RHS Green 137A.

*Strength*.—Moderate, flexible.

FLOWER

Not observed to date.

REPRODUCTIVE ORGANS

Not observed to date.

OTHER CHARACTERISTICS

Fruits and seeds: Not observed to date.

Disease/pest resistance: Neither resistance nor susceptibility to other normal diseases and pests of *Syngonium* observed.

Temperature range: About 5° C. to 40° C.

What is claimed is:

1. A new and distinct cultivar of *Syngonium* plant named 'CLA 20230912' as herein illustrated and described.

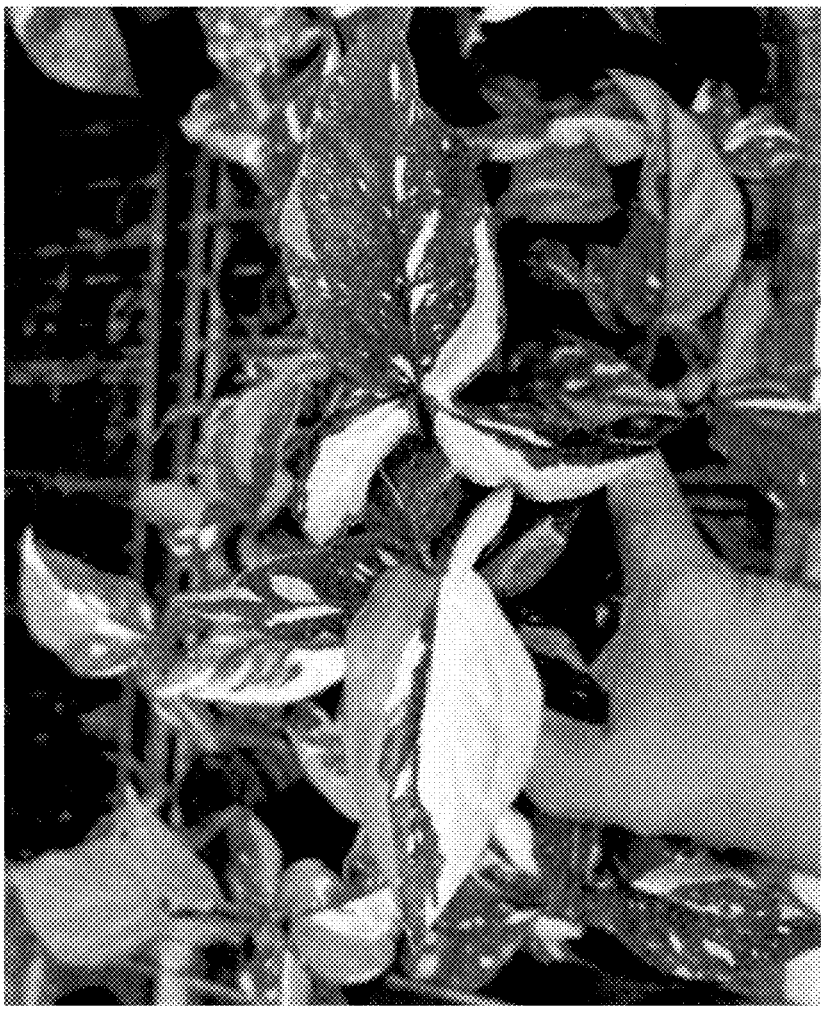

* * * * *